US00PP29723P2

(12) United States Plant Patent
Hansen

(10) Patent No.: US PP29,723 P2
(45) Date of Patent: Oct. 2, 2018

(54) **X *MANGAVE* PLANT NAMED 'CATCH A WAVE'**

(50) Latin Name: **Hybrid; x *Mangave* times *Agave***
Varietal Denomination: Catch a Wave

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/732,107

(22) Filed: Sep. 19, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new and unique X *Mangave* plant named 'Catch a Wave' characterized by a compact mound of bluish-green, thick, lanceolate, coarsely sinuate, folded to concaved foliage. Marginal and apical spines are soft and flexible. Leaves develop small, irregular, greyed-purple spots with strong ultra violet light. The new plants is suitable for the garden landscape or as a potted plant in the garden or around the home.

1 Drawing Sheet

Botanical classification: hybrid; x *Mangave* times *Agave*.
Variety denomination: 'Catch a Wave'.

BACKGROUND OF THE INVENTION

The present invention relates to the new and distinct X *Mangave* hybrid plant, X *Mangave* 'Catch a Wave' hybridized by the inventor at a wholesale perennial nursery in Zeeland, Mich., USA as cross between a proprietary, unreleased, hybrid known as X *Mangave* H10-2 (not patented) as the female or seed parent times an unnamed selection of *Agave colorata* (not patented) as the male or pollen parent. The cross was performed in the Apr. 10, 2012 and seeds were harvested and sown later on Aug. 1, 2012. Through trials at the same nursery the plant was originally assigned the breeder code XMANG-12-19-10. The new plant has been successfully asexually propagated initially by division at the same nursery in Zeeland, Mich. and also by sterile shoot-tip tissue culture. Both methods of asexual propagation systems have been found to produce stable and identical plants that maintain all the unique characteristics of the original plant.

No plants of X *Mangave* 'Catch a Wave' have been sold, under this or any name, in this country or anywhere in the world, prior to the filing of this application, nor has any disclosure of the new plant been made prior to the filing of this application with the exception of that which was disclosed or sold within one year of the filing of this application, and was either derived directly or indirectly from the inventor.

BRIEF SUMMARY OF THE INVENTION

X *Mangave* 'Catch a Wave' differs from its parents as well as all other *Manfreda, Agave* and X *Mangave* known to the applicant. Compared with the female parent the foliage of the new plant is shorter and more compact, the foliage is broader and thicker with larger marginal spines. Compared with the male parent the new plant has longer more lanceolate foliage with more dark green to purple-colored spotting and the teeth are not as hard. The most similar known cultivars are X *Mangave* 'Silver Fox' co-pending U.S. Plant Patent Application and X *Mangave* 'Tooth Fairy' co-pending U.S. Plant Patent Application. Compared with 'Silver Fox' the new plant has longer, less glaucous leaves that are more coarsely sinuate, with softer marginal spines and the coloration is less purple spotted. Compared with 'Tooth Fairy' the new plant has longer, more coarsely sinuate foliage that has smaller, softer and less pigmented marginal spines.

The new plant, 'Catch a Wave', is unique from each of the above cultivars and all *Agave*, X *Mangave* and *Manfreda* known to the inventor by the following combined traits:

1. Compact mound of thick, lanceolate, coarsely sinuate foliage, folded to concaved;
2. Bluish-green foliage develops heavy, irregular, greyed-purple spots with strong ultra-violet light;
3. Teeth on leaves are soft and very flexible;
4. Moderate to rapid growth rate.

BRIEF DESCRIPTION OF THE DRAWING

The drawing of x *Mangave* 'Catch a Wave' demonstrates the overall appearance of a three-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
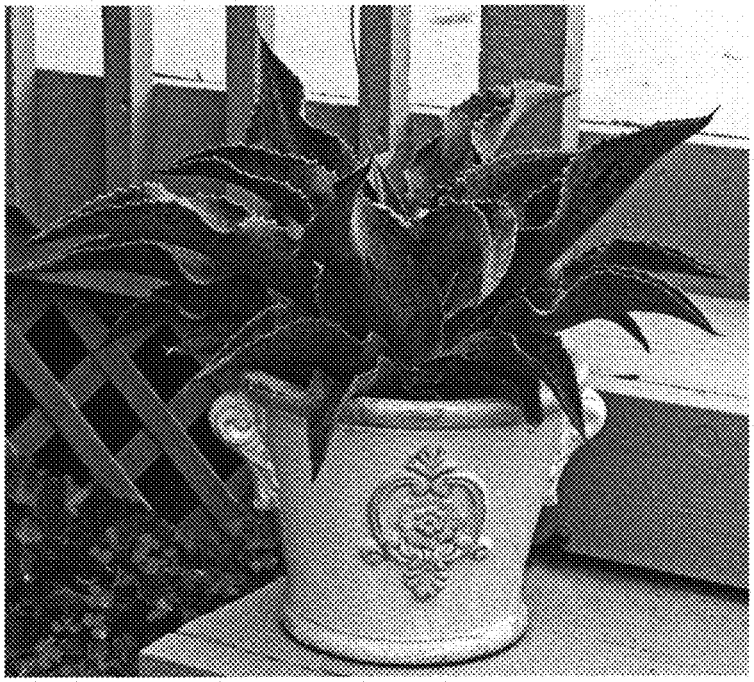
FIG. 1 shows a side view of the new plant foliage, marginal teeth and apical spines.
Figure 2:
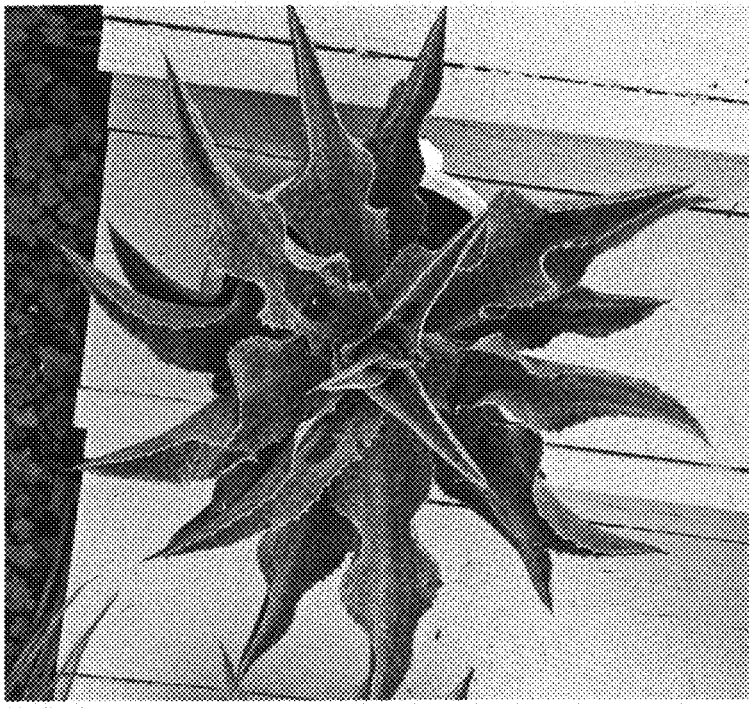
FIG. 2 shows a top view of the new plant showing the coarse wave of the leaves.

The following descriptions and color references are based on the 2015 edition of The Royal Horticultural Society Colour Chart except where common dictionary terms are used. The new plant, X *Mangave* 'Catch a Wave', has not been observed under all possible environments. The phenotype may vary slightly with different environmental conditions, such as temperature, light, fertility, moisture and maturity levels, but without any change in the genotype. The following observations and size descriptions are of a three-year-old plant in a commercial wholesale greenhouse in Zeeland, Mich. with supplemental water and fertilizer as needed.

Parentage: X *Mangave* H10-2 as female (seed) patent consisting of a proprietary unreleased *Manfreda maculosa* (not patented) times a proprietary unreleased *Agave gypsophila* (not patented) and *Agave colorata* as male (pollen) parent;

Propagation: Division of side shoots and sterile shoot-tip tissue culture;

Time to initiate roots from tissue culture: About 21 days;

Growth rate: Moderate to rapid;

Crop time: About 12 to 14 weeks to finish in a 3.8 liter container from a 35 mm tissue culture growing at about 21° C.;

Rooting habit: fleshy, lightly branching, with roots up to 15 cm long;

Root color: Variable depending on grow activity, and soil; between nearest RHS NN155C and RHS 161C;

Plant shape and habit: Succulent, frost-tender, herbaceous perennial with basal rosettes of about 16 leaves radially emerging outwardly from central stem, producing a radially-symmetrical, rounded mound;

Plant size: Foliage height about 50.0 cm tall from soil line to the top of the leaves and about 76.0 cm wide at the widest point slightly above soil line in container;

Foliage description: Lanceolate; simple; margins dentate with flexible teeth; thick; lightly glaucous abaxial and adaxial; glabrous abaxial and adaxial; teeth about 3.0 mm long and spaced about six teeth per 10 cm with flexible spine; apex acute with flexible terminal spine; truncate sessile base; partially conduplicate; coarsely sinuate; with greyed-purple spots about 1.0 mm to 3.0 mm in diameter;

Leaf size: To about 25.0 cm long, about 6.0 cm wide approximately two-thirds toward apex; and about 6.0 mm thick at base; average about 18.5 cm long, 4.8 cm wide and 5.5 mm thick;

Foliage fragrance: None observed;

Leaf blade color:

*Adaxial* (*young*).—Nearest RHS 138B with spots intensifying with ultraviolet light exposure from the sun to between RHS N187B and RHS N187A; Abaxial (young): nearest RHS N138B with spots intensifying with ultraviolet sunlight exposure to tinted between RHS N187B and RHS N187A.

*Adaxial* (*mature*).—Nearest RHS NN137A with light glaucous coating where not washed away, and with spots intensifying with ultraviolet sunlight exposure tinted between RHS N187B and RHS N187A; Abaxial (mature): blend between RHS 189A and RHS 138A with light glaucous coating where not washed away.

*Teeth*.—Nearest RHS 190B.

Petiole: Leaves sessile;

Veins: Parallel; not distinct abaxial or adaxial;

Inflorescence description: Upright panicle with flowers clustered at about 18 nodes; about 90 flowers in distal 48.0 cm of peduncle;

Peduncle: Terete; glabrous, glaucous; stiff; strong; erect; to about 176 cm tall and 2.0 cm diameter at base;

Peduncle color: Blend between RHS N187B and RHS N189C;

Peduncle bracts: Linear; narrowly acute apex; truncate clasping base; margin dentate with teeth about 1.0 mm long; about 21 bracts below flowers and about 18 flowering node bracts; to about 24.0 cm long and 3.0 cm wide in proximal region decreasing to about 30.0 mm long and 25.0 mm wide in distal region; drying before flower anthesis;

Peduncle bract color: Same as foliage before drying;

Pedicel: Terete; glaucous; glabrous; variable length from 2.0 mm to 4.0 mm long and about 3.0 mm diameter;

Pedicel color: Blend between RHS 146D and RHS 144A;

Buds one day prior to opening: Elongated globose with tube base; about 5.5 cm long and about 12.0 mm diameter mid-tepal and tube about 9.0 mm diameter;

Bud color: Basal two-thirds nearest RHS 146B and distal one-third strongly blushed with N187A;

Flower description: Perfect; campanulate; actinomorphic; about 9.5 cm long from base of ovary to tip of anthers and 2.3 cm wide at anthers and 18.0 mm wide at tip of tepals; with abundant sweet nectar;

Flower period: Individual flowers lasting up to 3 days; flowering when mature, frequently late winter to early spring under greenhouse conditions in Michigan; flowering for about three weeks;

Flower fragrance: Lightly sweet;

Tepals: Six in two sets of three; glaucous abaxial and slightly lustrous adaxial; glabrous both adaxial and abaxial; acute apex and fused base; outer set about 3.4 cm long and 9.5 mm wide at fusion, inner set about 3.3 cm long and 8.0 mm wide at fusion;

Tepal color: Outer set abaxial base nearest RHS 146B, distal 12.0 mm strongly blushed with RHS N187A, outer set adaxial base nearest RHS 145C, distal 12.0 mm strongly blushed with RHS N186C; inner set abaxial 1.0 mm margin blend between RHS 146D and RHS 152D, base blend between RHS 138A and RHS 144A, distally blend between RHS 167C and RHS 146D, inner set adaxial base nearest RHS 145C, distally blushed with nearest RHS N186C;

Androecium: Six;

*Filaments*.—Six; exserted; terete distally, slightly applanate proximally; stiff and straight; adnate to inner corolla in proximal 8.0 mm; to about 6.4 cm long and 1.5 mm diameter; color nearest RHS N186C in proximal 3.5 cm, transitioning to nearest RHS 155A heavily maculate in distal 15.0 mm with spots nearest RHS N186C.

*Anthers*.—Dorsifixed; longitudinal; tips curved backwards toward attachment point upon dehiscence; about 19.0 mm long and 2.0 mm wide; color between RHS 151D and RHS N144A and maculate with RHS N186C.

*Pollen*.—Abundant; color nearest RHS 6A.

Gynoecium: Inferior; 9.0 cm long;

*Style*.—Terete; glabrous; about 6.5 cm long and 2.0 mm diameter at base; color blend between RHS 151D and N144A maculate with nearest RHS N186C to nearly solid RHS N186C in proximal 3.5 cm.

*Stigma turbinate, apex tri-lobed*.—About 2.5 mm tall and 3.5 mm across; color nearest RHS 177B with top stigmatic surface nearest RHS 196A.

*Ovary*.—Inferior; ellipsoidal; slightly fluted; 1.5 cm long and 7.0 mm diameter in center: color blend between RHS 146D and RHS 144A.

Fruit and seed: Not observed;

Disease resistance: X *Mangave* 'Catch a Wave' has not been observed to be resistant to diseases beyond that which is normal for X *Mangave, Agave* or *Manfreda*. The new plant is xeromorphic and survives well with minimal water once established. The new plant is hardy to least USDA zone 10. Full extent of winter hardiness has not been tested.

It is claimed:

1. A new and distinct cultivar of ornamental X *Mangave* plant named 'Catch a Wave' as herein described and illustrated.

* * * * *